United States Patent [19]

Francese et al.

[11] Patent Number: 5,722,421
[45] Date of Patent: Mar. 3, 1998

[54] CLEVIS HAVING DEFLECTION LIMITING STOPS FOR USE IN AN ENDOSCOPIC BIOPSY FORCEPS INSTRUMENT

[75] Inventors: Jose L. Francese; Joel F. Giurtino; Matthew A. Palmer. all of Miami, Fla.

[73] Assignee: Symbiosis Corporation. Miami, Fla.

[21] Appl. No.: 528,767

[22] Filed: Sep. 15, 1995

[51] Int. Cl.[6] .................................................. A61B 10/00
[52] U.S. Cl. .................................. 128/751; 606/205
[58] Field of Search ............................ 128/749, 751, 128/752, 753, 754, 755, 756, 757; 606/205, 206, 207, 208, 209, 167, 170, 174

[56] References Cited

U.S. PATENT DOCUMENTS 5,228,451  7/1993  Bales et al. .
5,366,467  11/1994  Lynch et al. .

Primary Examiner—Vincent Millin
Assistant Examiner—Robert N. Wieland
Attorney, Agent, or Firm—Finnegan, Henderson, Farabow, Garrett and Dunner, L.L.P.

[57] ABSTRACT

A deflection-limiting clevis includes a substantially cylindrical base with a pair of clevis arms extending therefrom, a clevis axle extending between distal ends of the clevis arms and a pair of stops located on interior portions of the clevis arms between the base and the axle. The stops are dimensioned and located to engage respective tangs of a pair of jaws, which are mounted on the axle, when the jaws are deflected across the center line of the clevis. A first embodiment of the clevis may be used with or without a conventional flat needle between the jaws. In a second embodiment of the clevis, a cross member is located between the clevis arms proximal of the clevis axle and distal of the cylindrical base. The cross member may be used to engage the proximal end of a shortened flat needle which is mounted between the jaws and is also used to engage the tangs of the jaws when the jaws are rotated about the axle to a point of deflection. A third embodiment of the invention combines aspects of the first and second embodiments and includes both a pair of stops located on interior portions of the clevis arms between the base and the axle and a cross member located between the stops and the cylindrical base. The third embodiment allows allowing the use of a shortened flat needle while also allowing some deflection of the jaws.

18 Claims, 8 Drawing Sheets

CLEVIS HAVING DEFLECTION LIMITING STOPS FOR USE IN AN ENDOSCOPIC BIOPSY FORCEPS INSTRUMENT

BACKGROUND OF THE INVENTION

1. Field of the Invention

The invention relates to endoscopic biopsy forceps instruments. More particularly, the invention relates to a clevis which limits deflection of the forceps jaws in an endoscopic biopsy forceps instrument.

2. State of the Art

Endoscopic biopsy forceps are used for taking tissue samples from the human body for analysis. A typical biopsy forceps instrument is shown in prior art FIGS. 1–3 and 3a and disclosed in co-owned U.S. Pat. No. 5,228,451, the complete disclosure of which is hereby incorporated by reference herein. The biopsy forceps instrument 10 generally includes a proximal handle 12 and a distal end effector assembly 14. A long flexible coil 16 having a pair of axially displaceable control wires 18, 19 extending therethrough couples the handle 12 and the end effector assembly 14. The coil 16 is preferably covered with a PTFE, FEP or polyolefin sheath 15 along substantially all of its length and a strain relief sleeve 17 covering a portion of the coil which extends from the handle 12. The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The proximal end of the coil 16 is coupled to the distal end of the bore 26 in the handle 12. The displaceable spool 22 is provided with a cross member 30 which passes through the slot 28 in the central shaft 20. The cross member 30 is provided with a coupling means 32 for attaching the proximal ends of the control wires 18, 19. The end effector assembly 14 includes a clevis 34 which is coupled to the distal end of the coil 16, and a pair of forceps jaws 36, 38 which are rotatably mounted in the clevis 34 by means of an axle pin 40. Each jaw 36, 38 is provided with distal cutting teeth 36a, 38a and a proximal tang 36b, 38b. The proximal tangs 36b, 38b are each coupled to the distal end of a respective control wire 18, 19.

From the foregoing, those skilled in the art will appreciate that relative movement of the shaft 20 and spool 22 results in movement of the control wires 18, 19 relative to the coil 16. Such action results in opening and closing of the jaws 36, 38 as shown in prior art FIGS. 2 and 3. More particularly, when the jaws are moved from the open position to the closed position, the jaw 36 moves clockwise toward the center line CL of the clevis 34 as the jaw 38 moves counter-clockwise toward the center line CL. When closed, the jaws meet at or about the center line CL of the clevis 34.

The endoscopic biopsy procedure is accomplished through an endoscope which is inserted into a body and guided by manipulation to the biopsy site. The endoscope typically includes a long narrow flexible tube with an optical lens and a narrow lumen for receiving a biopsy forceps. The practitioner guides the endoscope to the biopsy site while looking through the optical lens and inserts the biopsy forceps through the lumen of the endoscope to the biopsy site. The path of the endoscope to the biopsy site is usually long and tortuous. As the distal end of the forceps instrument passes through turns in the endoscope, the closed jaws may be deflected across the centerline CL in a direction as shown, for example, in FIG. 4. While the amount of deflection may not be as great as shown in FIG. 4, it will be appreciated that the only thing that prevents the jaws 36, 38 from being deflected across the centerline, as shown in FIG. 4, is the tension applied to the control wires 18, 19. While a certain amount of deflection may be desirable to avoid damage to the interior of the endoscope, excessive deflection can damage the forceps instrument. In extreme retroflexed conditions or when taking a sample sideways, the amount of deflection shown in FIG. 4 is possible. When deflection is excessive the control wires may become kinked, tangled, or disconnected from the jaws thereby preventing the jaws from operating properly when they arrive at the biopsy site. Moreover, if the jaws are severely deflected, they can become stuck in the deflected position, and the interior of the lumen of the endoscope may be scraped and damaged as the deflected jaws pass out of the turn and through a straight portion of the endoscope.

After the jaws are delivered to the biopsy site, the practitioner manipulates the actuating handle to effect a tissue sampling operation at the distal end of the instrument while viewing the biopsy site through the optical lens of the endoscope. After a sample has been obtained, the practitioner and/or an assistant carefully withdraws the instrument from the endoscope while holding the actuating handle to maintain the jaws in a closed position lest the sample be lost inside the endoscope. As the instrument is withdrawn from the endoscope, the danger of deflection of the jaws is again present.

Another type of biopsy forceps instrument which is known in the art and disclosed in the above-referenced co-owned patent is shown in prior art FIGS. 5–7. This instrument is substantially the same as the instrument described above, but with a slightly different end effector assembly 14a. Here, a flat needle (or knife) 37 is disposed between the jaws 36, 38. The needle 37 has a sharp distal end 37a which terminates within the jaws 36, 37 when they are closed as shown in FIG. 6. The needle 37 has a proximal end 37b which extends partially into the distal end of the coil 16, and a central portion 37c which has an opening through which the axle pin 40 passes. The location of the proximal end 37b of the needle 37 prevents it from rotating about the axle pin 40. It will be appreciated that the end effector assembly 14a is somewhat protected from excessive jaw deflection by the presence of the needle 37. For example, as the jaws become deflected as shown in prior art FIG. 7, the needle 37 may prevent the jaws from deflecting more than a few degrees. However, given the relative mass of the jaws versus the needle, it is possible that deflection of the jaws will not be prevented by the needle and that the needle will be damaged by the jaws. Moreover, it is possible that the control wires 18, 19 will become tangled on the proximal end of the needle even after an acceptable amount of jaw deflection.

SUMMARY OF THE INVENTION

It is therefore an object of the invention to provide a deflection-limiting clevis for use in a biopsy forceps instrument to prevent excessive deflection of the jaws when they are in the closed position.

It is also an object of the invention to provide a deflection-limiting clevis for use in a biopsy forceps which permits some deflection of the jaws when they are in the closed position.

It is another object of the invention to provide a deflection-limiting clevis for use in a biopsy forceps instrument having an end effector assembly which includes a needle and jaws.

It is still another object of the invention to provide a deflection-limiting clevis for use in a biopsy forceps instrument which operates in conjunction with existing jaws.

It is also an object of the invention to provide a deflection-limiting clevis for use in a biopsy forceps instrument in conjunction with a needle which eliminates or reduces the possibility of control wires becoming tangled on the proximal end of the needle.

In accord with these objects which will be discussed in detail below, a first embodiment of the clevis of the present invention includes a substantially cylindrical base with a pair of clevis arms extending therefrom, a clevis axle extending between distal ends of the clevis arms and a pair of stops located on interior portions of the clevis arms between the base and the axle. The stops are dimensioned and located to engage respective tangs of a pair of jaws, which are mounted on the axle, when the jaws are rotated about the axle to a point of deflection. The stops are therefore preferably located and dimensioned to allow some deflection and to prevent excessive deflection; although it is possible to arrange the stops so that substantially no deflection is permitted. The first embodiment of the clevis may be used with or without a conventional flat needle between the jaws.

In a second embodiment of the clevis, a cross member is located between the clevis arms proximal of the clevis axle and distal of the cylindrical base. The cross member may be used to engage the proximal end of a shortened flat needle which is mounted between the jaws and is also used to engage the tangs of the jaws when the jaws are rotated about the axle to a point of deflection. The second embodiment allows substantially no deflection of the jaws.

A third embodiment of the invention combines aspects of the first and second embodiments and includes both a pair of stops located on interior portions of the clevis arms between the base and the axle and a cross member located between the stops and the cylindrical base. The third embodiment allows the use of a shortened flat needle while also allowing some deflection of the jaws.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
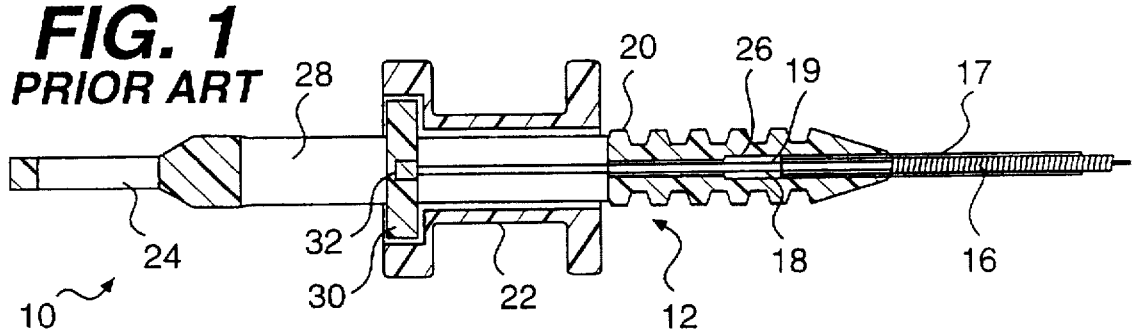
FIG. 1 is a broken side elevation view in partial section of the proximal end of a prior art biopsy forceps instrument.
Figure 2:
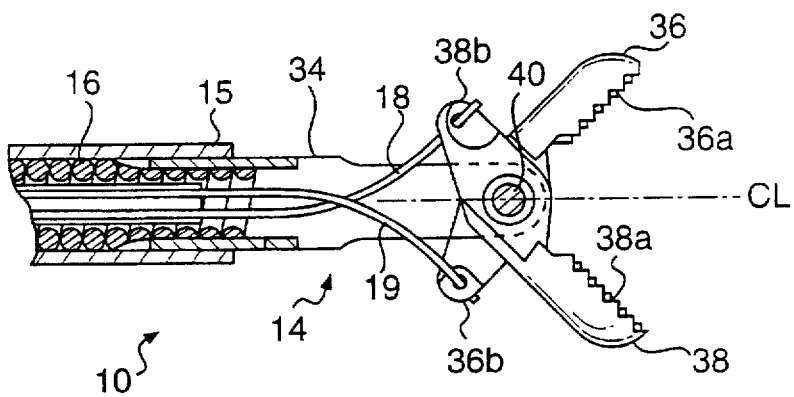
FIG. 2 is an enlarged broken side elevation view in partial section of the distal end of a prior art biopsy forceps instrument with the jaws in the open position.
Figure 3:
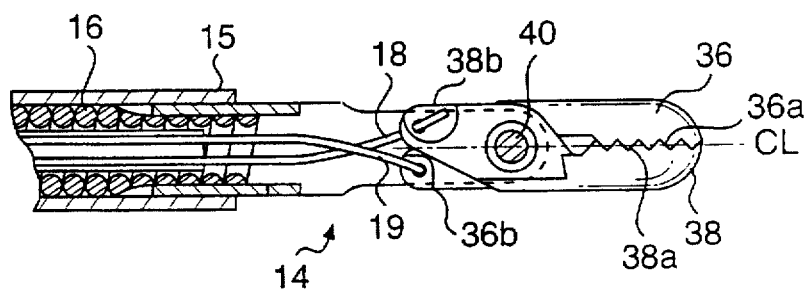
FIG. 3 is an enlarged broken side elevation view in partial section of the distal end of a prior art biopsy forceps instrument with the jaws in the closed position.
Figure 3A:
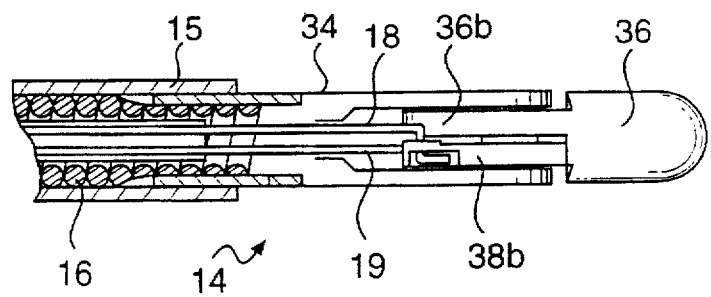
FIG. 3a is an enlarged broken top view in partial section of the distal end of a prior art biopsy forceps instrument with the jaws in the closed position.
Figure 4:
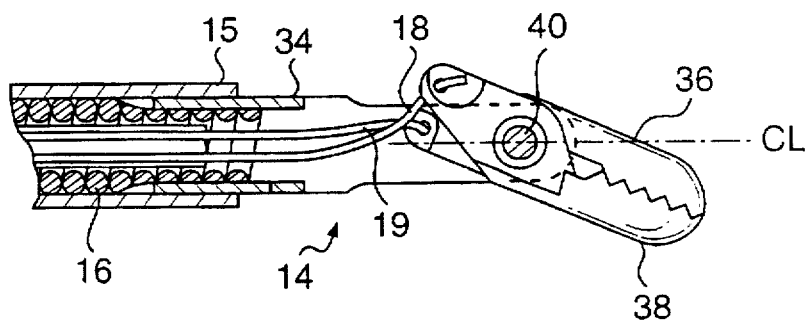
FIG. 4 is a view similar to FIG. 3 showing the jaws of a prior art biopsy forceps instrument excessively deflected.
Figure 5:
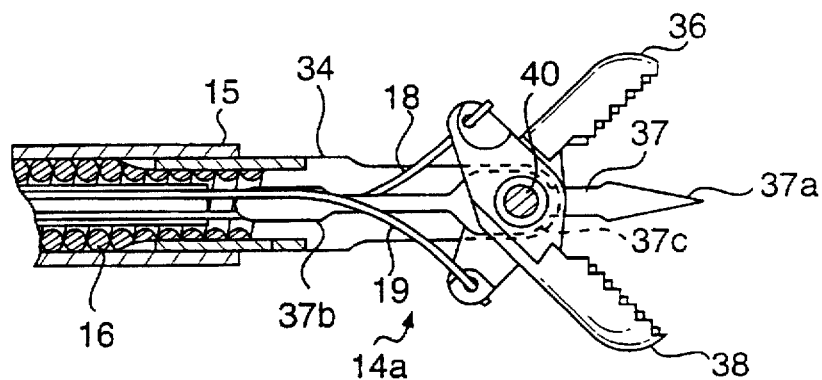
FIG. 5 is a view similar to FIG. 2 of the distal end of another prior art biopsy forceps instrument.
Figure 6:
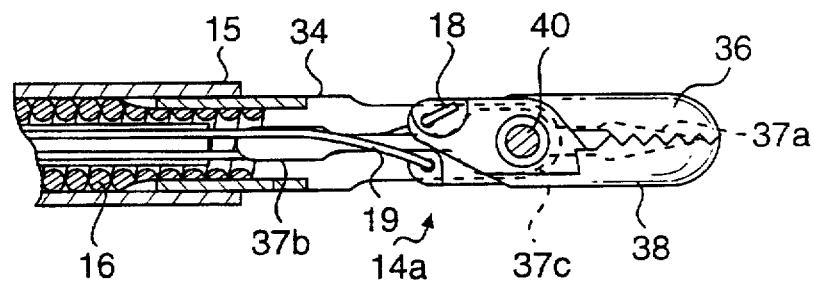
FIG. 6 is a view similar to FIG. 3 of the prior art biopsy forceps instrument of FIG. 5.
Figure 7:
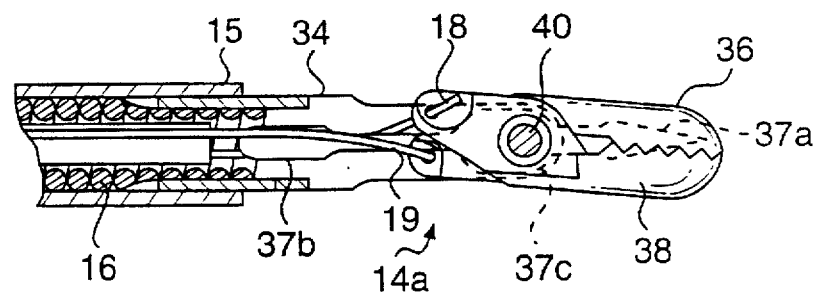
FIG. 7 is a view similar to FIG. 4 of the prior art biopsy forceps instrument of FIGS. 5 and 6.
Figure 8:
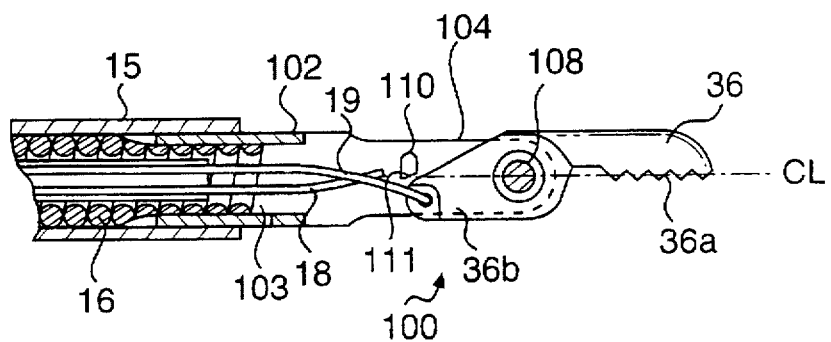
FIG. 8 is a view similar to FIG. 3 of the distal end of a biopsy forceps instrument incorporating a first embodiment of the invention with one jaw removed for clarity.
Figure 8A:
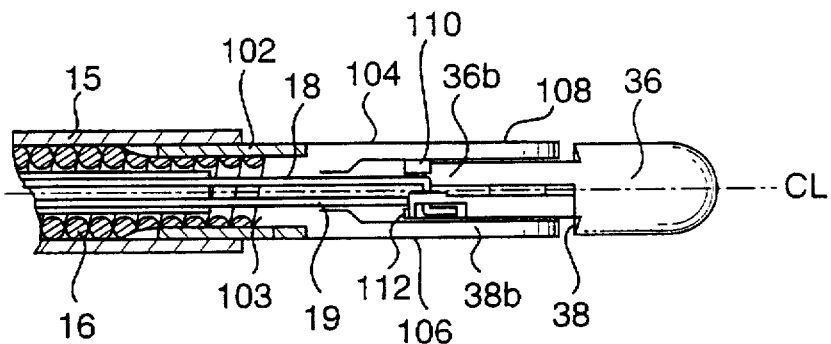
FIG. 8a is a view similar to FIG. 3a of the distal end of a biopsy forceps instrument incorporating the first embodiment of the invention.
Figure 8B:
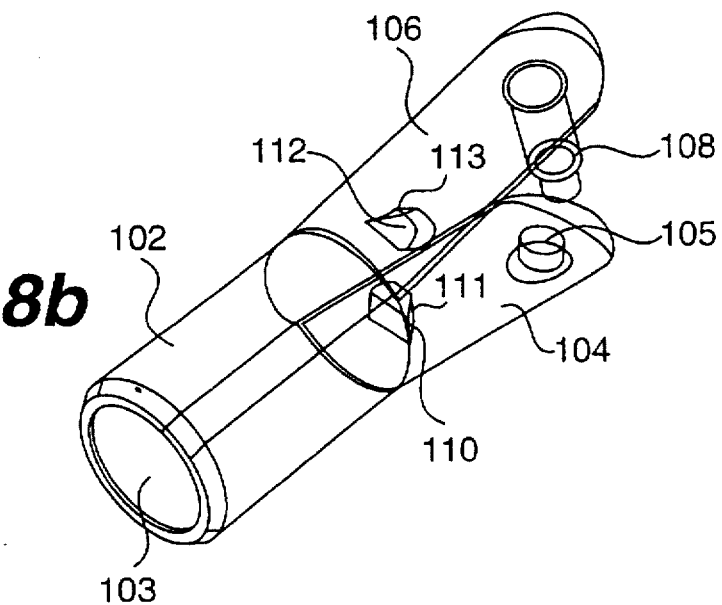
FIG. 8b is a transparent perspective view of the first embodiment of the invention.
Figure 8C:
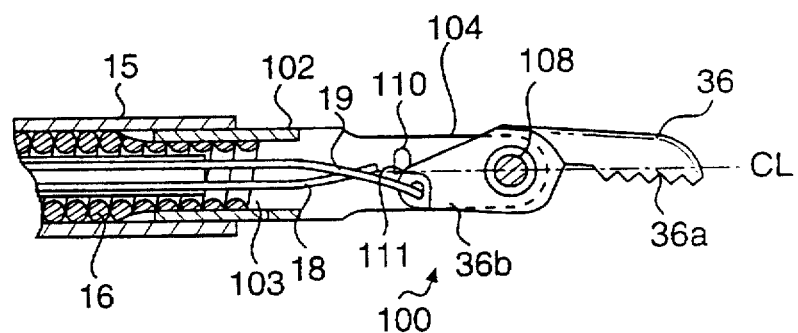
FIG. 8c is a view similar to FIG. 8 showing a permitted amount of deflection of a forceps jaw.
Figure 8D:
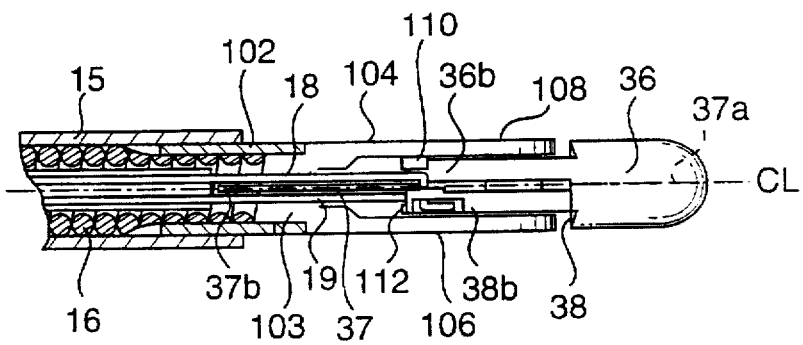
FIG. 8d is a view similar to FIG. 8a showing the first embodiment of the clevis of the invention in conjunction with a conventional flat needle.

Referring now to FIGS. 8 and 8a–8d, a first embodiment of the clevis 100 according to the invention includes a cylindrical base member 102, a pair of clevis arms 104, 106 which extend distally from the base member, a clevis axle 108 which extends between the distal ends of the clevis arms, and a pair of stops 110, 112 which extend inward from the inner surfaces of the clevis arms at a location proximal of the axle 108. The cylindrical base member 102 has a central bore 103 which extends into the space between the arms 104, 106. According to a presently preferred embodiment, the clevis axle extends inward from one of the arms, e.g. 106, and the other arm, e.g. 104, is provided with a hole 105 which receives the end of the clevis axle 108 as described in more detail below. Each of the stops 110, 112 is provided with an engaging surface 111, 113 which faces a dorsal portion of a respective jaw tang 36b, 38b when conventional jaws 36, 38 are mounted in the clevis 100. Comparing FIGS. 8 and 8c, it will be appreciated that the location of the engaging surfaces 111, 113 of the stops 110, 112, determines the amount of the jaw deflection which is permitted by the stops. For example, as shown in FIG. 8c, the jaw 36 is permitted to deflect a few degrees downward across the center line CL of the clevis 100 before a dorsal portion of its tang 36b is engaged by the surface 111 of the stop 110. From the foregoing, those skilled in the art will appreciate that if the stops are axially symmetrical as suggested by FIG. 8b, the jaw 38 will be permitted to deflect a similar amount upward across the center line CL before a dorsal portion of the tang 38b is engaged by the surface 113 of the stop 112. As mentioned above, it will be understood that the terms "upward" and "downward" are used relatively in reference to the Figures shown. As seen best in FIGS. 8a and 8d, the stops 110, 112 extend inward from the arms of 104, 106 but do not pass the centerline CL of the clevis 100. This assures that the stops do not interfere with the opening of the jaws and permits the use of a conventional flat needle 37 with the clevis 100 as shown in FIG. 8d. The stops and their engaging surfaces may be dimensioned in several ways to accommodate different types of jaws and to permit different amounts of deflection.

Figure 9:
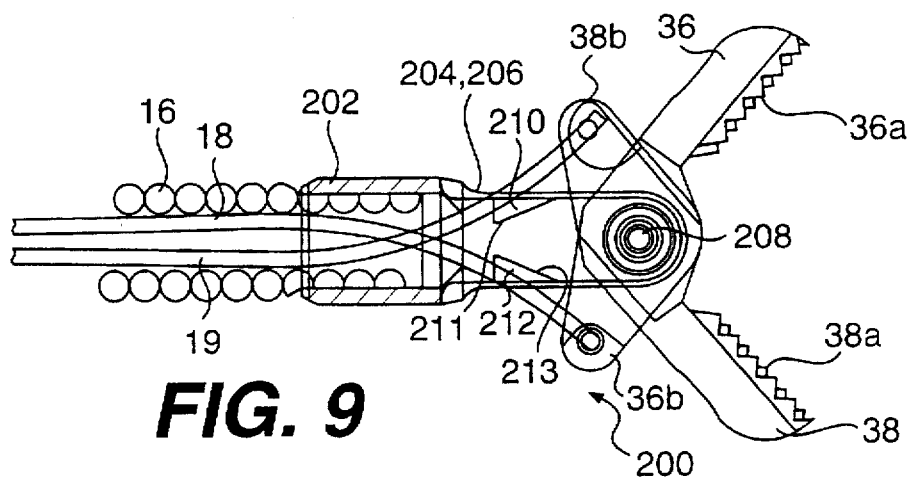
FIG. 9 is a view similar to FIG. 2 of an alternate first embodiment of the invention with forceps jaws in the open position.
Figure 9A:
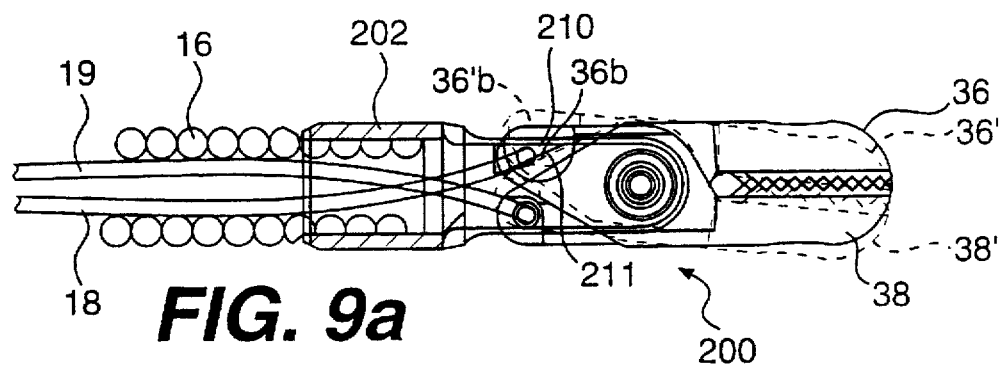
FIG. 9a is a view similar to FIG. 9 with jaws in the closed position and with phantom lines showing a permitted amount of deflection of the closed jaws.

FIGS. 9 and 9a–9c show a variation on the first embodiment of the clevis of FIGS. 8 and 8a–8d. The clevis 200 of FIGS. 9 and 9a–9c is substantially the same as the clevis 100 described above and similar reference numerals (incremented by 100) refer to similar elements of the clevis 200. Here, however, the engaging surfaces 211, 213 of the respective stops 210, 212 are broader and shallower than the surfaces 111, 113 shown in FIGS. 8, 8b, and 8c. By making the surfaces broader and shallower, an increased amount of deflection can be permitted. For example, as shown in FIG. 9a, the jaw 36 is permitted to deflect downward several degrees from horizontal to the position shown by the phantom lines and labelled 36'. When the jaws 36, 38 are in the closed position, the jaw 38 is similarly restrained from downward deflection beyond the position shown by the phantom lines 38'. The downward deflection of the jaws is limited by the broad flat engaging surface 211 of the stop 210 which engages a dorsal portion of the tang 36b of the jaw 36 when it is deflected to the position shown at 36b. It will be appreciated that deflection of the jaw 38 upward from horizontal will be similarly limited by the engaging surface 213 which will engage a dorsal portion of the tang 38b of the jaw 38.

Figure 9B:
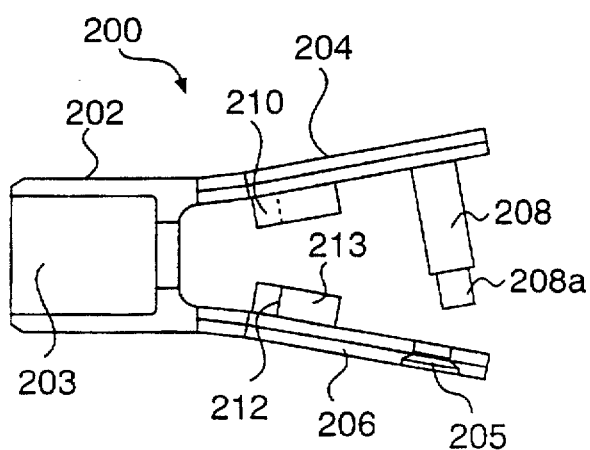
FIG. 9b is a top view of a the clevis of FIGS. 9 and 9a in an open position prior to mounting the jaws on the clevis.
Figure 9C:
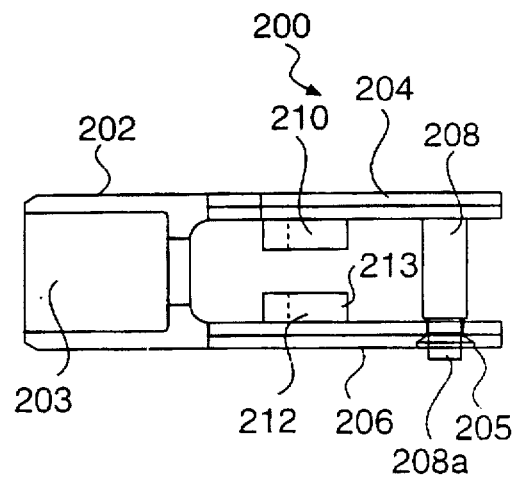
FIG. 9c is a view similar to FIG. 9b, but in the closed position.

Referring now to FIGS. 9b and 9c, a presently preferred embodiment of the clevis 200 is a unitary molded member which includes a clevis axle 208 extending from one of the arms, e.g. 204, and a axle receiving hole 205 is provided in the other arm, e.g. 206. The arms 204, 206 are bendable so that the jaws 36, 38 can be mounted on the axle 208 when the arms are spread apart as shown in FIG. 9b. After the jaws are mounted on the axle 208, the arms are bent together to the position shown in FIG. 9c so that the free end 208a of the axle 208 extends through the hole 205 in the arm 206. The free end 208a of the axle 208 is then spread to form a rivet-like coupling. It will be understood, however, that the essence of the invention lies in the deflection-limiting stops and not in the clevis axle. Therefore, the clevis axle may just as well be formed as a separate piece and each arm of the clevis may then be provided with a hole for receiving the axle in a conventional manner.

Turning now to FIGS. 10, and 10a–10e, a second embodiment of a clevis according to the invention is shown. The clevis 300 is similar to the clevises described above in that it has a cylindrical base member 302, a pair of clevis arms 304, 306, and a clevis axle 308. The clevis 300 does not have a spaced pair of stops, however. Instead, a cross member 309 (which may be formed from two pieces as described below) is provided between the arms 304, 306 at a location proximal of the axle 308. The cross member 309 is preferably wedge or tear-drop shaped having an upper distal engaging stop surface 313 and a lower distal engaging stop surface 311. The clevis 300 is particularly well suited for use with a shortened flat needle 337. The needle 337 is similar to a conventional needle having a sharp distal end 337a and a central mounting portion 337c. The proximal end 337b of the needle 337 terminates closer to the clevis axle 308 than a conventional needle and therefore does not enter the distal end of the coil 16. Moreover, the proximal end 337b of the needle 337 is provided with a notch 337d which is engaged by the distal engaging surfaces 311, 313 of the cross member 309. The cross member 309, therefore maintains the needle 337 in a stable position along the centerline of the clevis 300 without requiring the proximal end of the needle to enter the distal end of the coil 16 or the cylindrical base 302 of the clevis 300. This yields the advantage that the proximal end of the needle is not in a position to interfere with the control wires 18, 19. In addition, as seen best in FIG. 10a, the cross member 309 acts as a deflection limiting stop for the jaws 36, 38. When the jaws are closed, a dorsal portion of the tang 36b is substantially engaged by the engaging surface 311 and a dorsal portion of the tang 38b is substantially engaged by the engaging surface 313. The stopping action of the cross member 309 thus permits substantially no deflection of the jaws 36, 38. From the foregoing, those skilled in the art will appreciate that in order to achieve the needle location advantage described above and yet provide for some allowable jaw deflection, it would be necessary to redesign the jaw tangs 36b, 38b and/or make the cross member 309 smaller in size. Since this could substantially weaken the cross member, this embodiment is best suited for applications where substantially no deflection is desired.

Figure 10:
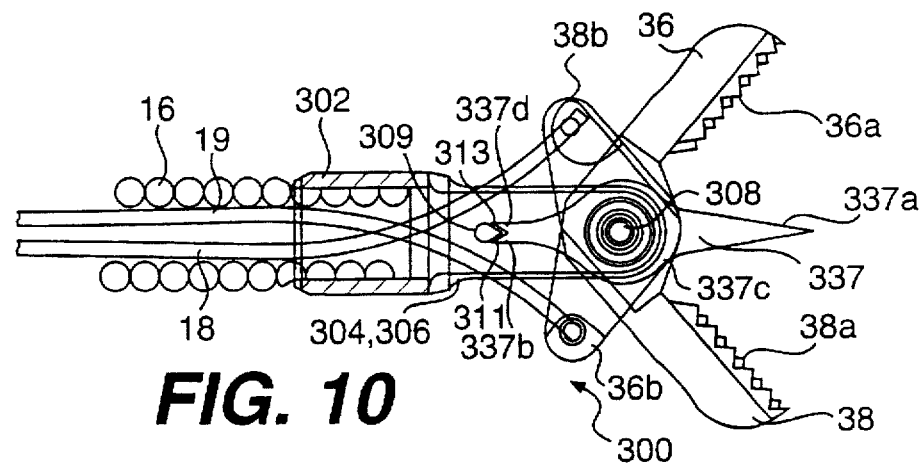
FIG. 10 is a view similar to FIG. 9 of a second embodiment of the invention in conjunction with a shortened flat needle.
Figure 10A:
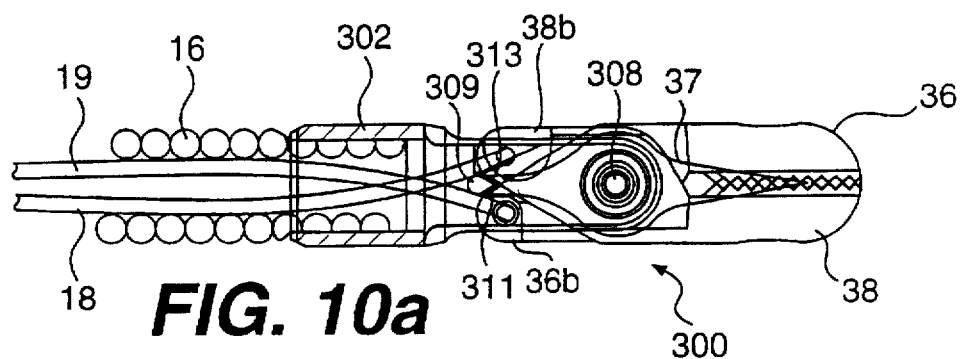
FIG. 10a is a view similar to FIG. 9a of the second embodiment of the invention.
Figure 10B:
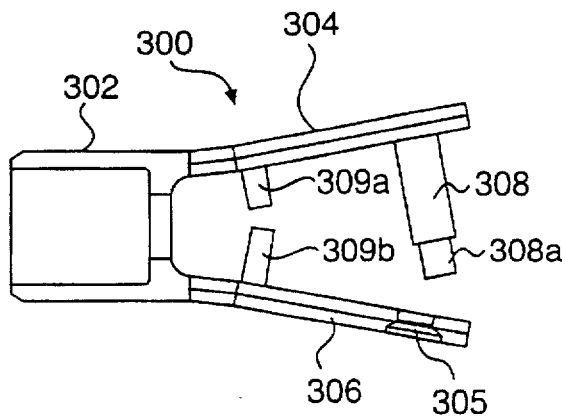
FIG. 10b is a view similar to FIG. 9b of the second embodiment of the invention.
Figure 10C:
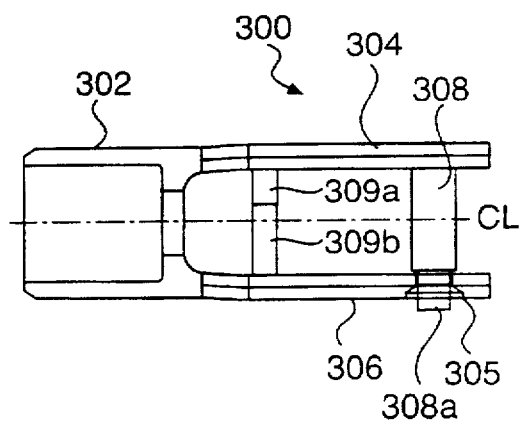
FIG. 10c is a view similar to FIG. 9c of the second embodiment of the invention.

The clevis 300 is preferably manufactured and assembled in substantially the same manner as the clevis 200 described above. FIGS. 10b and 10c show the similarity of construction as compared to FIGS. 9b and 9c. Due to the location of the cross member 309, it is preferably molded as two pieces 309a, 309b, each extending from a respective arm 304, 306 as shown in FIG. 10b. When the arms are bent together as shown in FIG. 10c, the ends of the respective pieces 309a, 309b are brought together to form the cross member 309 which extends between the arms 304, 306. As seen best in FIG. 10c, the pieces 309a and 309b are preferably of unequal length so that they join each other at a location off of the centerline CL of the clevis 300. This is to assure that the proximal end 337b of the needle 337 does not engage the cross member 309 at the point where the two pieces 309a, 309b join, a point which might be weak due to minor errors in molding the clevis. It will be appreciated, however, that the clevis 300 can be made without the integral axle 308. In that case, the cross member 309 could be formed as a single piece. Moreover, it will be appreciated that the cross member 309 could be made as a piece separate from the clevis 300 and inserted through the clevis in a manner similar to the insertion of a separate clevis axle.

Figure 10D:
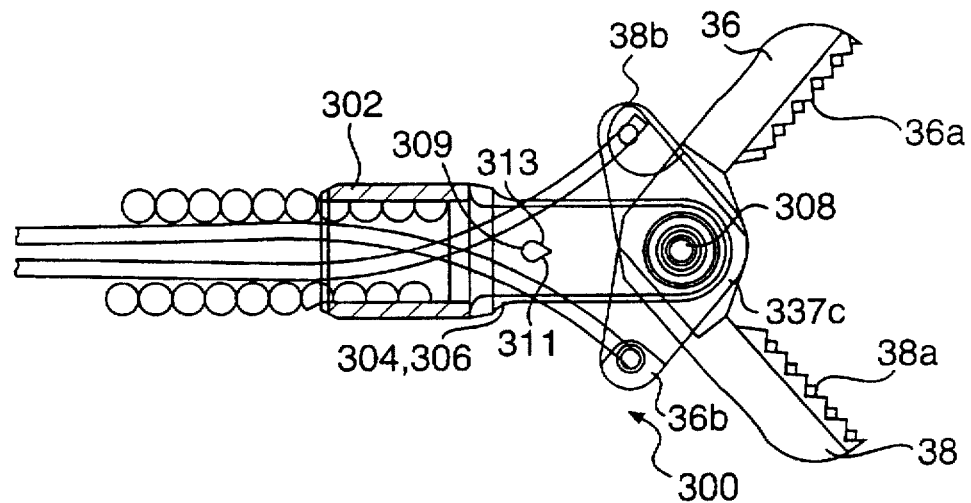
FIG. 10d is a view similar to FIG. 10 of the second embodiment of the invention without the needle.
Figure 10E:
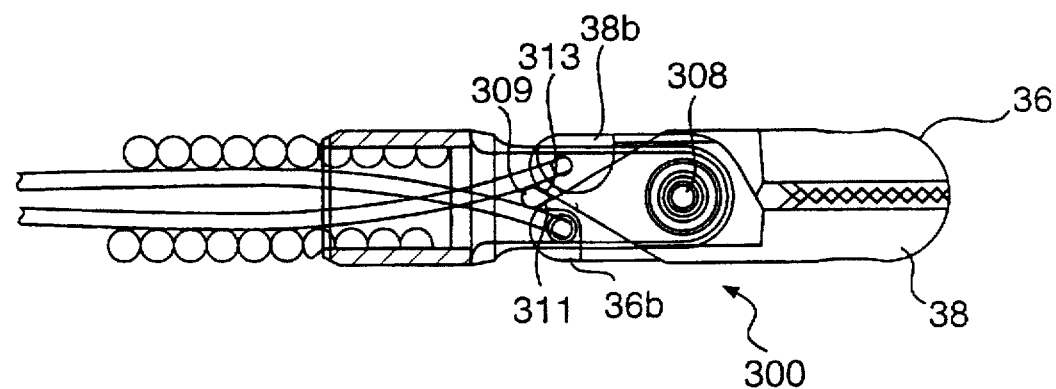
FIG. 10e is a view similar to FIG. 10a of the second embodiment of the invention without the needle.

As shown in FIGS. 10d and 10e, the clevis 300 does not require the use of a needle and may be used with jaws 36, 38 to provide substantially zero deflection, if desired, as described above.

Figure 11:
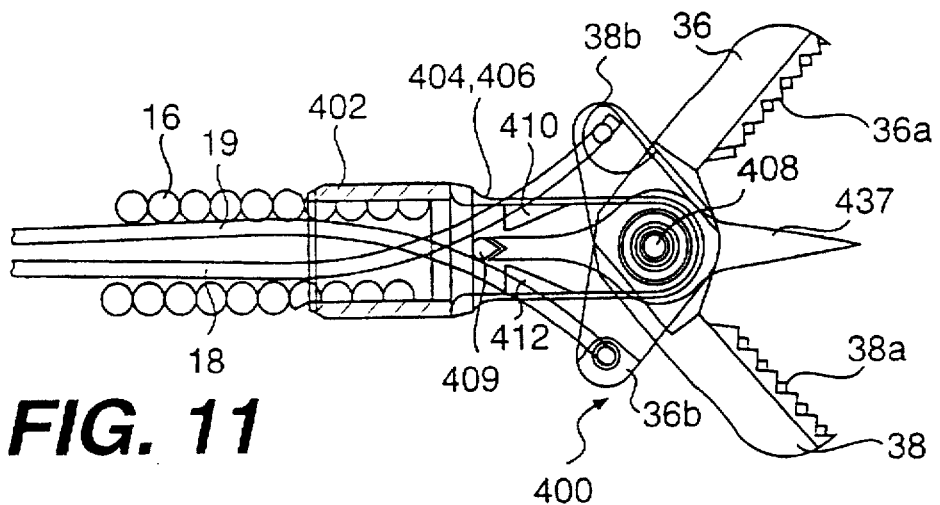
FIG. 11 is a view similar to FIG. 9 of a third embodiment of the invention in conjunction with a shortened flat needle.
Figure 11A:
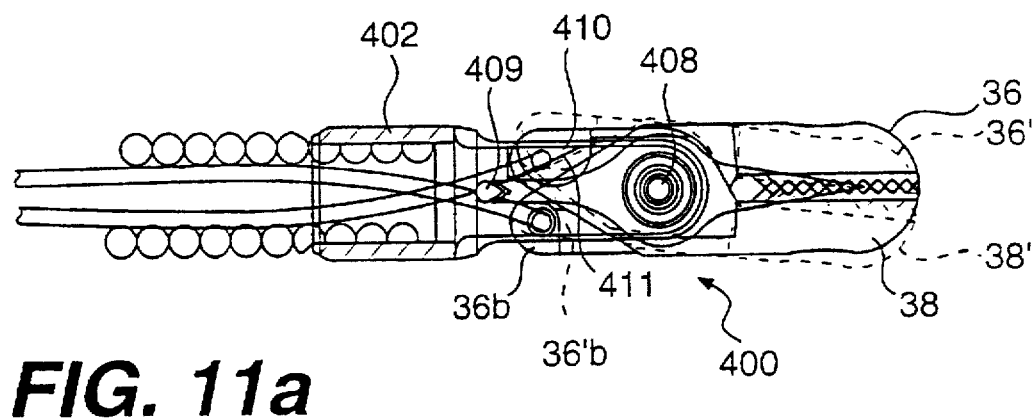
FIG. 11a is a view similar to FIG. 9a of the third embodiment of the invention.
Figure 11B:
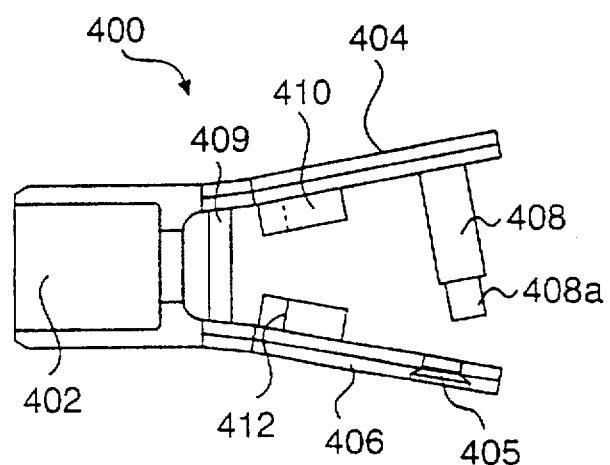
FIG. 11b is a view similar to FIG. 9b of the third embodiment of the invention.

A third embodiment of a clevis 400, shown in FIGS. 11, 11a, and 11b seeks to obtain the needle location advantage described above and yet provide for some allowable jaw deflection. This is achieved by relocating the cross member 409 closer to the cylindrical base 402 of the clevis 400 and by providing a pair of stops 410, 412 distal of the cross member 409. By properly dimensioning the clevis 400 and a needle 437, the cross member 409 and the proximal end of the needle 437 can be located distal of the cylindrical base 402, yet proximal of the stops 410, 412 and the tangs 36b, 38b of the jaws 36, 38. Therefore, as shown in FIG. 11a, the cross member 409 is removed from a position where it interferes with jaw deflection. The jaws 36, 38 are permitted to deflect to the position shown in phantom and labelled 36', 38' until they are stopped by the stop 410 as described above.

The clevis 400 may be manufactured in the substantially same manner as described above and as illustrated in FIG. 11b. The relocation of the cross member 409 allows it to be made as a single piece since it is proximal of the portions of the arms 404, 406 which bend outward. Alternatively and as suggested above, the cross member may be added to the clevis as a separate piece which is inserted through holes in the clevis arms.

There have been described and illustrated herein several embodiments of a clevis having deflection limiting stops. While particular embodiments of the invention have been described, it is not intended that the invention be limited thereto, as it is intended that the invention be as broad in scope as the art will allow and that the specification be read likewise. Thus, while particular locations and shapes of stops have been disclosed, it will be appreciated that other locations and shapes could be utilized. Also, while particular modes of manufacture have been disclosed, it will be recognized that other modes of manufacture could be used with similar results obtained. It will therefore be appreciated by those skilled in the art that yet other modifications could be made to the provided invention without deviating from its spirit and scope as so claimed.

We claim:

1. A deflection-limiting clevis for use in an endoscopic instrument having a pair of jaws, each jaw having a proximal tang for coupling the jaw to a control wire, said clevis comprising:
   a) a substantially cylindrical base;
   b) first and second clevis arms extending distally from said base, each of said first and second clevis arms having an interior surface and a distal end;
   c) a clevis axle extending perpendicularly between said first and second clevis arms near their distal ends, and on which the jaws are mounted so that the tangs of the jaws extend proximally of said clevis axle; and
   d) at least one stop extending from said interior surface of one of said first and second clevis arms toward said interior surface of another of said first and second clevis arms, said at least one stop being located proximal of said clevis axle and distal of said base and having at least one engaging surface for engaging the tang of at least one of the jaws to limit deflection of the at least one of the jaws when the jaws are in a closed position.

2. A deflection-limiting clevis according to claim 1, wherein:
   said at least one stop comprises a first stop having a first engaging surface and a second stop having a second engaging surface,
   said first stop extending from said interior surface of said first clevis arm toward said interior surface of said second clevis arm,
   said second stop extending from said interior surface of said second clevis arm toward said interior surface of said first clevis arm, and
   said first engaging surface for engaging the tang of one of the jaws and said second engaging surface for engaging the tang of the other of the jaws.

3. A deflection-limiting clevis according to claim 2, wherein:
   said first engaging surface and said second engaging surface are located to allow some deflection of the jaws across a center line of said clevis before engaging the tangs of the jaws.

4. A deflection-limiting clevis according to claim 2, wherein:
   said first engaging surface and said second engaging surface are located to allow substantially no deflection of the jaws across a center line of said clevis before engaging the tangs of the jaws.

5. A deflection-limiting clevis according to claim 1, wherein:
   said at least one stop comprises a cross member extending between said first and second clevis arms.

6. A deflection-limiting clevis according to claim 5, wherein:
   said cross member has a substantially wedge shaped cross-sectional profile defining an upper distal engaging surface and a lower distal engaging surface.

7. A deflection-limiting clevis according to claim 2, for use in an endoscopic instrument having a flat needle for mounting between the pair of jaws, the needle having a proximal end, said clevis further comprising:
   e) a cross member extending between and coupled to said first and second clevis arms at a location proximal of said first and second stops, said cross member for engaging the proximal end of the needle.

8. A deflection-limiting clevis according to claim 7, wherein:
   said cross member has a substantially wedge shaped cross-sectional profile and the proximal end of the needle has a notch which is engaged by said cross member.

9. A deflection-limiting clevis according to claim 5, wherein:
   said cross member is formed from first and second parts, said first part extending from said first clevis arm and said second part extending from said second clevis arm.

10. An endoscopic biopsy forceps instrument comprising:
    a) a flexible coil having a proximal and a distal end;
    b) at least one control wire having a proximal and a distal end and extending through said flexible coil;
    c) actuation means coupled to said proximal end of said flexible coil and said proximal end of said at least one control wire for displacing one of said flexible coil and said at least one control wire relative to the other;
    d) a clevis having a substantially cylindrical base which is coupled to said distal end of said flexible coil and first and second clevis arms which extend distally from said substantially cylindrical base, each of said first and second clevis arms having an interior surface;
    e) a clevis axle extending perpendicularly between said first and second clevis arms;
    f) a pair of forceps jaws, each of said jaws being rotatably mounted on said clevis axle and having a proximal tang coupled to said distal end of said at least one control wire, wherein
    said clevis further includes at least one deflection-limiting stop extending from said interior surface of one of said first and second clevis arms toward said interior surface of another of said first and second clevis arms, said at least one stop being located proximal of said clevis axle and distal of said base and having at least one engaging surface for engaging said tang of at least one of said jaws to limit deflection of said at least one of the jaws when said jaws are in a closed position.

11. An endoscopic biopsy forceps instrument according to claim 10, wherein:

said at least one stop comprises a first stop having a first engaging surface and a second stop having a second engaging surface, said first stop extending from said interior surface of said first clevis arm toward said interior surface of said second clevis arm, said second stop extending from said interior surface of said second clevis arm toward said interior surface of said first clevis arm, and said first engaging surface for engaging said tang of one of said jaws and said second engaging surface for engaging said tang of the other of said jaws.

12. An endoscopic biopsy forceps instrument according to claim 11, wherein:

said first engaging surface and said second engaging surface are located to allow some deflection of said jaws across a center line of said clevis before engaging said tangs of said jaws.

13. An endoscopic biopsy forceps instrument according to claim 11, wherein:

said first engaging surface and said second engaging surface are located to allow substantially no deflection of said jaws across a center line of said clevis before engaging said tangs of said jaws.

14. An endoscopic biopsy forceps instrument according to claim 10, wherein:

said at least one stop comprises a cross member extending between said first and second clevis arms.

15. An endoscopic biopsy forceps instrument according to claim 14, wherein:

said cross member has a substantially wedge shaped cross-sectional profile defining an upper distal engaging surface and a lower distal engaging surface.

16. An endoscopic biopsy forceps instrument according to claim 14, further comprising:

g) a flat needle having a sharp distal end, a central mounting hole, and a notched proximal end, said flat needle being mounted on said clevis axle and said notched proximal end being engaged by said cross member.

17. An endoscopic biopsy forceps instrument according to claim 16, wherein:

said cross member has a substantially wedge shaped cross-sectional profile for engaging said notched proximal end.

18. An endoscopic biopsy forceps instrument according to claim 14, wherein:

said cross member is formed from first and second parts, said first part extending from said first clevis arm and said second part extending from said second clevis arm.

* * * * *